United States Patent [19]

Faulkner et al.

[11] Patent Number: 5,376,129
[45] Date of Patent: Dec. 27, 1994

[54] METHOD AND APPARATUS FOR MAKING PROSTHETIC SOCKET PREFORMS, PROSTHETIC SOCKETS, AND SOCKET ATTACHMENT COMPONENT

[75] Inventors: Virgil W. Faulkner; Nicolas E. Walsh, both of San Antonio, Tex.

[73] Assignee: Board of Regents, The University of Texas System, Austin, Tex.

[21] Appl. No.: 621,992

[22] Filed: Dec. 4, 1990

[51] Int. Cl.⁵ .......................... A61F 2/60; A61F 2/78; A61F 2/68; A61F 2/80
[52] U.S. Cl. ........................................ 623/33; 623/31; 623/32; 623/38
[58] Field of Search ................... 623/30, 31, 32, 33, 623/34, 35, 36, 37, 38

[56] References Cited

U.S. PATENT DOCUMENTS

| | | | |
|---|---|---|---|
| 4,186,449 | 2/1980 | Horvath | 623/38 |
| 4,529,332 | 7/1985 | Glabiszewski | 623/38 X |
| 4,923,472 | 5/1990 | Ugolini | 623/38 X |
| 4,938,775 | 7/1990 | Morgan | 623/38 X |
| 5,062,849 | 11/1991 | Schelhas | 623/38 X |
| 5,116,382 | 5/1992 | Steinkamp et al. | 623/38 |

FOREIGN PATENT DOCUMENTS 2216455 11/1989 United Kingdom .

OTHER PUBLICATIONS

Coombes et al., "Memory Plastics for Prosthetic and Orthotic Applications," *Prosthetics and Orthotics International*, 12:143-151, Dec. 1988.

Greenwood et al., "Application of Memory Plastics to the Production of Prostheses," Report 1986 *Bio-Engineering Center Roe Hampton University College*, London, 47-51, 1986.

Staros et al., "Veterans Administration Prosthetics Center Research Report," *Bulletin of Prosthetics Research*, 232-242, Spring 1970.

Walsh et al., "A Computerized System to Manufacture Prostheses for Amputees in developing Countries," *Journal of Prosthetics and Orthotics*, vol. 1, 3:165-181, Apr. 1989.

Wilson et al., "A Material for Direct Forming of Prosthetic Sockets," *Artificial Limbs*, vol. 14, 1:53-56, Spring 1970.

*Primary Examiner*—Randall L. Green
*Assistant Examiner*—Dinh X. Nguyen
*Attorney, Agent, or Firm*—Arnold, White & Durkee

[57] ABSTRACT

A method and apparatus for making prosthetic socket preforms, a method for making prosthetic sockets, and a socket attachment component are disclosed. The method of making preforms of the present invention involves the blowmolding of memory plastics with a cooling step prior to parison expansion to enhance the molded-in stresses of the resulting preform. The blowmolding apparatus of the present invention comprises two mold halves having specially designed knifing sections and a modified blow pin. The method for making prosthetic sockets involves heat- and vacuum-forming memory plastic preforms over a positive cast of a residual limb after preheating of the cast to prevent heat-sinking. The socket attachment component disclosed is adapted for molding with a prosthetic socket during heat- and vacuum-forming, is configured to receive a sleeve attachment shaft, and possesses an integral male member for attaching the component and socket to an artificial limb shaft using bolts or screws.

6 Claims, 11 Drawing Sheets

METHOD AND APPARATUS FOR MAKING PROSTHETIC SOCKET PREFORMS, PROSTHETIC SOCKETS, AND SOCKET ATTACHMENT COMPONENT

BACKGROUND OF THE INVENTION

The present invention relates generally to methods and apparatus for making prosthetic devices for humans and specifically prosthetic socket preforms, prosthetic sockets and prosthetic socket attachment components. More particularly, the present invention concerns the fabrication of prosthetic socket preforms of memory plastic material using a blowmolding technique and the heat- and vacuum-forming of such preforms onto a positive cast of a residual limb to form a prosthetic socket. Further, the invention relates to a prosthetic socket attachment component molded within such a prosthetic socket for joining together a limb sleeve, the prosthetic socket and an artificial limb shaft.

Often, a prosthesis is required to assist in restoring an amputee's ability to accomplish many of life's daily tasks. In the case of lower extremity amputations such as the loss of a leg, the prosthesis allows the amputee to stand, walk and run by providing a mechanical extension to the residual limb or stump. Such a prosthesis may comprise an artificial foot connected to an artificial limb shaft with a custom-fitted socket and an elastic sleeve at one end which fits over the residual limb for securing the socket to the residual limb. One of the most important aspects of these prostheses is socket design, the socket being the load-bearing interface between the residual limb and the mechanical support system.

Because each socket must be custom-fitted to the individual patient, socket design and fabrication have been heretofore quite expensive and time-consuming. One technique commonly used to make prosthetic sockets has been to drape a sheet of heated plastic over a positive cast of the residual limb, manually forming the plastic to conform to the contours of the cast. This technique, known as "drape-forming" usually requires two persons and a large degree of manual skill. Further, it often results in significant amounts of wasted plastic and nonuniform forming.

Another technique previously disclosed has been to provide a generally conical, hollow socket preform of memory plastic material which is then placed over a positive cast of the residual limb, the combination being placed in an oven and heated sufficiently to induce shrinkage of the preform onto the cast surface to create a semi-finished socket. This technique, known as "shrink-forming," takes advantage of the characteristics of such memory plastic materials, in particular their tendency to return to their original shape when reheated. This method has been described in an article entitled "Memory plastics for prosthetic and orthotic applications," A. Coombes, C. Greenwood, *Prosthetics and Orthotics International*, v. 12, pp. 143-155 (1988) and also in "A Computerized System to Manufacture Prostheses for Amputees in Developing Countries," N. Walsh, J. Lancaster, V. Faulkner, W. Rogers, *Journal of Prosthetics and Orthotics*, v. 1, n. 3, pp. 165-181 (April, 1989). The contents of these two publications is incorporated herein by reference.

Although shrink-forming offers a more efficient, less labor- and skill-intensive method of socket fabrication than drape-forming, the basic method as described above suffers from several problems. First, the preform may develop imperfections or even perforations during heating at the points of initial contact with the positive cast. This is due to the temperature differential between the cast and the preform during heating, with the cast acting as a heat sink at these points of initial contact. Second, the conventional convection-type ovens presently used in shrink-forming result in nonuniform heating of the preform which in turn results in nonuniform shrinkage of the preform over the cast. Finally, the degree of shrinkage of presently available preforms is less than optimal for these purposes, although this deficiency may be somewhat compensated for by applying a vacuum to the preform/cast interface to help conform the preform to the contours of the cast.

It is believed that the root of the last-mentioned problem lies not so much with the shrink-forming technique but rather with the preform itself. A particularly advantageous method of producing the socket preform utilizes blowmolding, offering fewer steps than other techniques such as injection molding. The use of blowmolding to form socket preforms is also disclosed in the above-referenced articles. Blowmolding in such an application involves extruding heated plastic through a mandrel and die to form a parison or tube, enclosing the parison within a mold, and injecting air into the parison until it expands to conform to the contours of the inner cavity of the mold. The use of standard blowmolding techniques, however, does not produce a preform product with optimal shrinkage characteristics. Further, standard blowmolding molds often produce an undesirable raised portion or rib on the inner surface of the preform at its upper end. Because of its location, this rib is difficult to remove and often creates a non-uniform area in the final product. Finally, conventional molds also suffer from parison severing at the upper mold interface during blowmolding of plastics that have a high melt flow index.

One further problem affecting presently available socket technology relates to the mode of attaching the socket and the residual limb sleeve to the artificial limb shaft. In a typical configuration presently in use, the limb sleeve and socket are attached to the socket through a sleeve attachment device molded within the socket. A separate socket attachment plate is then molded or otherwise attached to a holding frame for the socket. This plate has a male or female attachment means that mates with artificial limb shaft. This configuration, requiring multiple parts and multiple assembly steps, adds additional expense to the already costly prosthesis and increases the likelihood of component failure under repeated loads.

Accordingly, it is desirable to provide a method and apparatus for reliably producing a socket preform with improved geometry and shrinkage characteristics. It is further desirable to provide a method of forming sockets from preforms which avoids the problems of nonuniform heating and heat-sinking by the cast. Finally, it is desirable to provide a simpler and more cost-effective means for attaching the prosthetic socket to the residual limb sleeve and artificial limb shaft.

SUMMARY OF THE INVENTION

The present invention provides an apparatus and method for making prosthetic socket preforms with improved geometry and shrinkage characteristics through blowmolding of memory plastic materials. Specifically, a mold for blowmolding prosthetic socket preforms is provided comprising first and second mold halves. Each mold half has a knifing section at its upper end, a blow pin aperture half at its lower end and an inner cavity located between the knifing section and the blow pin aperture half and dimensioned to form a socket preform of preselected dimensions from an expanded parison. The knifing section of each of the mold halves comprises a pinch-off zone for severing an upper portion of the parison, a clamping zone located below the pinch-off zone for securing the parison to the upper end of the mold halves, and a well located below the clamping zone for receiving excess plastic at the upper portion of the parison. This design offers a marked improvement over conventional molds. First, the clamping zone provides a solution to the problem of premature parison severing. Second, the well feature allows the excess plastic material that would form an internal rib in the preform using a standard mold to instead form an external rib which can be easily removed.

The blowmolding apparatus of the present invention for use with the mold of the present invention includes a plastic supply means for supplying memory plastic under pressure, and an extruding assembly operatively connected to the plastic supply means and operatively aligned with the upper end of the mold halves for extruding a tube of heated memory plastic material between the mold halves to form a parison. In one embodiment, the extruding assembly comprises a mandrel and die, the die being axially movable about the mandrel. The apparatus further comprises a blow pin operatively connected to a pressurized air source, aligned with the lower ends of the mold halves and extending into the mold cavity. In one preferred embodiment, the blow pin has an inlet passage for injecting air into the parison and a selectively closeable outlet passage for allowing air to exit from the parison.

The blowmolding method of the present invention comprises the following steps: First, a mold and blowmolding apparatus such as described above are provided, the mold halves being operatively aligned with the blow pin and the mandrel and die. Next, a tube of memory plastic material at a preselected temperature is extruded through the mandrel and die to form a parison, the parison extending between the mold halves through the mold cavity and out the lower end of the mold halves.

The blow pin is inserted into the lower end of the parison and the mold halves are moved together whereby the parison is pinched at its upper portion by a pinch-off zone of the knifing section of the upper area of the molds and is compressed at its lower portion around the blow pin by the blow pin aperture halves to form a substantially air-tight inner mold cavity. The parison is then cooled for a preselected time. In a preferred embodiment, the parison is cooled using the blow pin described above by injecting cooler air through the inlet passage to cool the inner surface of the parison and allowing the air to escape through the pin's outlet passage. The cooling step enhances the molded-in stresses in the resulting preform and thus enhances the shrinkage of the preform upon reheating. Next, air is injected through the blow pin into the sealed parison whereby the air pressure within the parison is increased until the parison has expanded to conform to the inner cavities formed by the mold halves, thus forming an unfinished socket preform. After the socket preform is allowed to cool for a preselected time in contact with the inner cavities of the mold halves, the mold halves are moved apart and the unfinished socket preform is removed and finished.

The present invention also provides an improved method of making a prosthetic socket from a plastic preform. This method comprises first making a positive cast of a patient's residual limb, the cast having an inner chamber open to the base of the cast and connected to a series of holes distributed over the exterior surface of the cast. The cast is then placed on a vacuum forming platform. The next step involves preheating the cast and platform. This minimizes the temperature differential between the cast/platform and the preform and thus avoids the heat-sinking effects of the prior art. In a preferred embodiment, an infra-red oven having evenly distributed radiation sources is used, which offers a significant improvement in heating uniformity over conventional ovens.

After preheating the cast and platform, the preform is placed over the cast and heated in the oven to shrink the preform over the exterior surface of the cast. A partial vacuum may be applied to the inner chamber of the cast to further conform the preform with the exterior surface of the cast to form a prosthetic socket. This method, which improves upon the method of shrink-forming, is referred to herein as heat- and vacuum-forming.

The present invention further provides a socket attachment component for integral molding with a prosthetic socket for attaching the prosthetic socket to an artificial limb shaft and for attaching the socket to a residual limb sleeve by means of a sleeve attachment shaft connected to the sleeve. In a particular embodiment, the component has a cylindrical body with a depression in its upper surface, a first cylindrical hollow or bore extending downward from the center of the depression for receiving a sleeve attachment shaft and a second cylindrical hollow intersecting the first cylindrical hollow and opening to the side surface of the body. A spring loaded pin is disposed in the second hollow, having a first end located proximate the first hollow for selectively engaging the sleeve attachment shaft and a second end located outside the second hollow. Finally, the socket attachment component has a male member extending from the lower surface of the body for engaging the artificial limb shaft. The two parts are secured by bolts or screws radially extending into the mating artificial limb shaft.

The socket attachment component may be integrally formed with the socket by placing the component atop the positive cast, the male member directed upward, under the preform, prior to shrink-forming. During heating, the preform will conform not only to the contours of the cast but also to the component, thus attaching the component to the socket.

In fitting a patient with a prosthesis incorporating the socket attachment component of the present invention, an elastic limb sleeve is slipped over the patient's residual limb, forming a partial vacuum with the limb for securing the sleeve to the limb. A sleeve attachment shaft is connected to the end of the limb sleeve. The sleeve and sleeve attachment shaft are then inserted into the socket, with the sleeve attachment shaft extending into the first hollow of the socket attachment component while the spring-loaded pin is retracted out of the first hollow. After the sleeve attachment shaft is fully inserted into the first hollow of the socket attachment component, the spring-loaded pin is released, which allows it to engage a notch in the sleeve attachment shaft, thus locking the sleeve and sleeve attachment shaft into place.

So that the manner in which the above recited features and advantages of the present invention, as well as others which will become apparent, are attained and can be understood in detail, more particular description of the invention, summarized above, may be had by reference to the embodiments thereof which are illustrated in the appended drawings, which drawings form a part of this specification.

It is to be noted, however, that the appended drawings illustrate only a typical embodiment of the invention and are therefore not to be considered limiting of its scope, for the invention may admit to other equally effective embodiments.

DETAILED DESCRIPTION OF THE PREFERRED EMBODIMENTS

It will be understood that the present invention can be practiced in a number of different ways within the scope of the claims appended hereto. The presently preferred embodiments will now be described.

Figure 1:
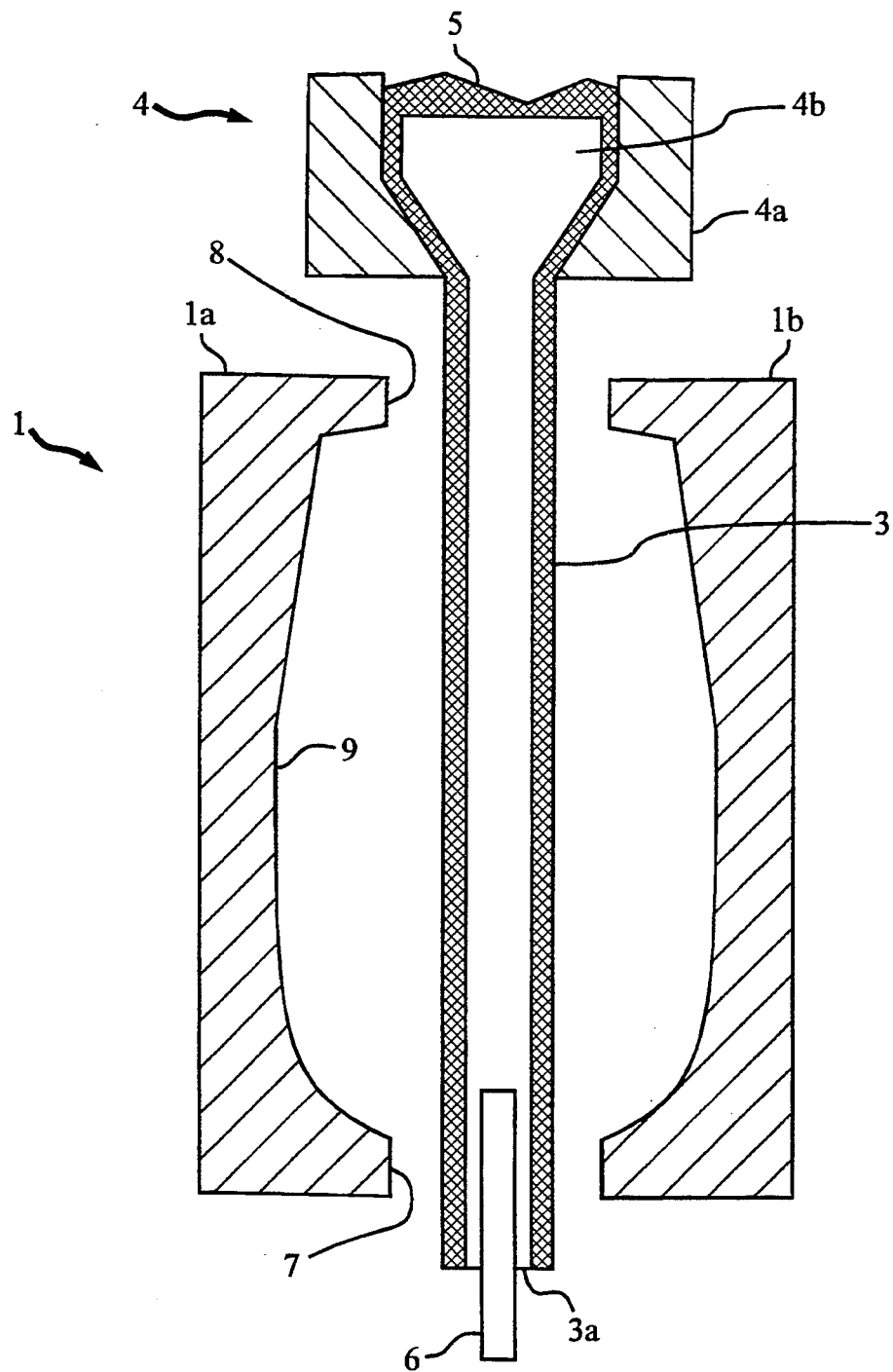
FIG. 1 is a sectional side view of the blowmolding apparatus and preform mold of the present invention.

Referring to FIG. 1, the apparatus used in the blowmolding method of the present invention and the mold of the present invention are shown in sectional side view. The mold 1 comprises first and second mold halves 1a and 1b. In a presently used embodiment, these mold halves are substantially symmetric. Each mold half has a knifing section 8 at its upper end, a blow pin aperture half 7 at its lower end and an inner cavity 9 located between the knifing section 8 and the blow pin aperture half 7. The blow pin aperture halves 7 each comprise a vertical channel substantially in the shape of a half-cylinder dimensioned to form a cylindrical passage for insertion of the blow pin 6 when the mold halves 1a and 1b are positioned together. The inner cavities 9 are dimensioned to form a socket preform of preselected dimensions from an expanded parison 3 when the mold halves 1a and 1b are moved together.

The blowmolding apparatus of FIG. 1 includes an extruding assembly 4 operatively connected to a plastic supply means (not shown) for extruding a tube 3 of heated memory plastic material 5, the tube extending between the mold halves 1a and 1b to form a parison 3 having an opening 3a at its lower end. In a particular embodiment, the extruding assembly 4 comprises a circular die 4a and mandrel 4b, the die 4a being axially movable about the mandrel 4b. The extruding assembly 4 is axially aligned with the upper portion of the mold halves 1a and 1b. The plastic supply means is capable of supplying molten memory plastic 5 to extruding assembly 4 under pressure at variable temperatures. The molding apparatus may further include a blow pin 6 having its lower end connected to a pressurized air source (not shown) and axially aligned with the lower end of the mold halves 1a and 1b. The blow pin 6 is located at the bottom of the mold 1 to minimize disruption of the upper portion of the preform.

Figure 2:
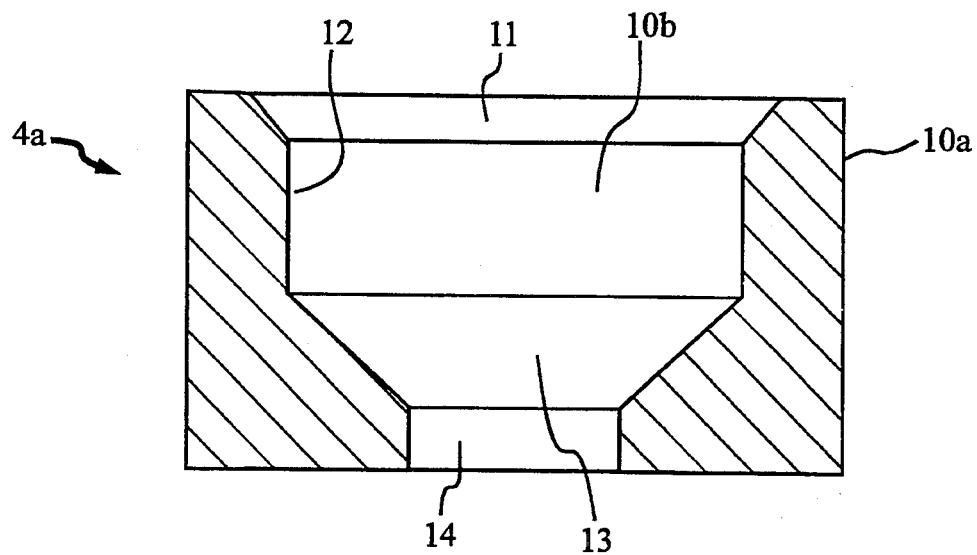
FIG. 2 is a sectional side view of the die used in the blowmolding method of the present invention.
Figure 2A:
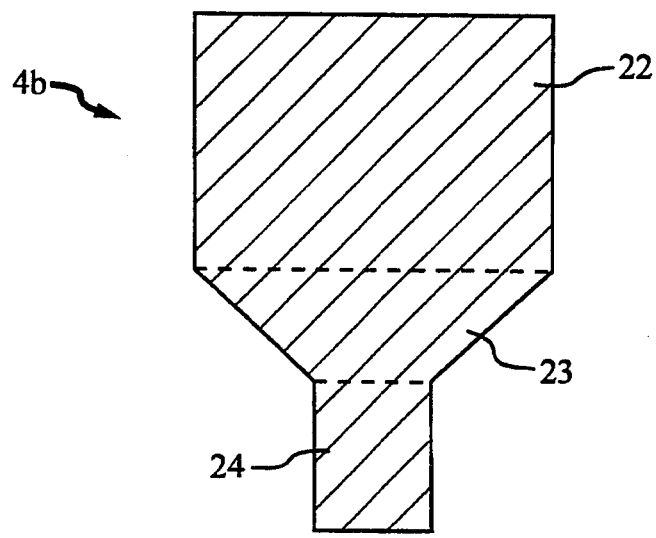
FIG. 2A is a sectional side view of the mandrel used in the blowmolding method of the present invention.

Sectional side views of the die 4a and the mandrel 4b are given in FIGS. 2 and 2A. The die 4a comprises a hollow cylindrical body 10a having an axial bore 10b opening to the upper and lower surfaces of the die 4a. Bore 10b includes a first frustoconical (tapered) portion 11 having its base at the upper surface of the die 4a, a first cylindrical portion 12 aligned with the frustoconical portion 11, a second frustoconical portion 13 having its base aligned with the first cylindrical portion 12, and a second cylindrical portion 14 aligned with the second frustoconical portion 13 and terminating at the lower surface of the die 4a such that a stepped funnel-like bore is formed. The mandrel 4b has a solid body having a first cylindrical portion 22 at its upper end, a frustoconical portion 23 having its base aligned with the first cylindrical portion 22, and a second cylindrical portion 24 at the lower end of the mandrel 4b aligned with the frustoconical portion 23. The die 4a and the mandrel 4b are dimensioned and the axial position of the die 4a in relation to the mandrel 4b is adjusted in such a manner as to create a parison having the desired inner and outer diameters. It should be understood that the extruding assembly 4 is but one example of a means for forming a parison 3 and other means may be employed to form a parison 3 without departing from the present invention.

Examples of certain desired preform wall thicknesses (outer preform diameter minus inner preform diameter) for selected plastics are given in TABLE 1, which also lists the blowmolding process conditions. The process conditions listed in TABLE 1 correspond to conditions presently used in connection with a blowmolding system. These conditions may vary from system to system. The optimal times and temperatures have been determined largely through trial and error.

In a particular embodiment, the parison wall thickness may be adjusted by a servo-valve system, such as a Hartig MR35 to compensate for thinning of the parison at large diameters. In particular, the servo-valve system controls the flow of molten plastic into the extruding assembly 4. The mandrel 4b is raised or lowered within the die 4a according to preset (programmed) commands to create thicker or thinner parison wall diameters. In this configuration, the outer diameter of the parison remains constant while the inner diameter is varied. For example and without limitation, a mandrel/die combination of 24/28 mm may be used for BK (below-knee) sockets, except for sockets of styrene butadiene copolymer, where a 28/32 mm mandrel/die combination is preferred. (The first number refers to the diameter of the second cylindrical portion 24 of the mandrel 4b and the second number refers to the diameter of the second cylindrical portion 14 of the chamber 10 of the die 4a.) The latter geometry may also be used for AK (above-knee) sockets. Different mandrel/die combinations and different parison wall thicknesses may be appropriate for other blowmolding systems.

Figure 3:
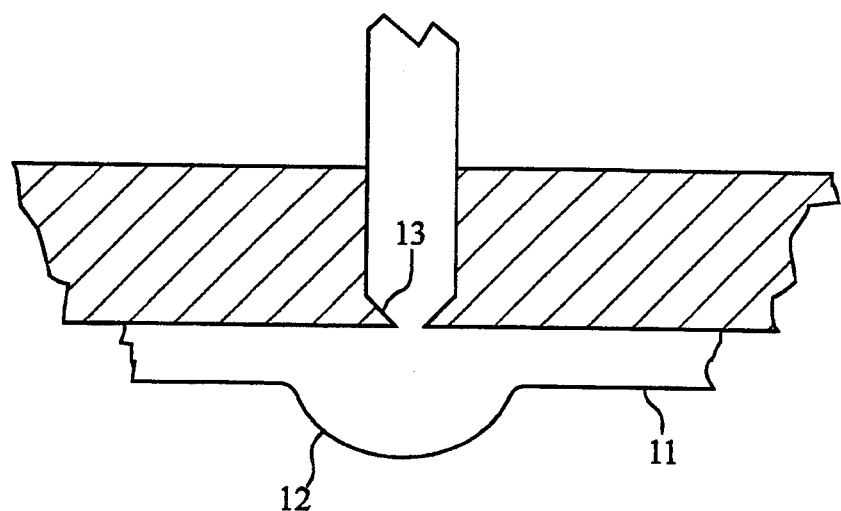
FIG. 3 is a sectional side view of the knifing section of a conventional blowmolding mold and resulting inner preform rib.
Figure 4:
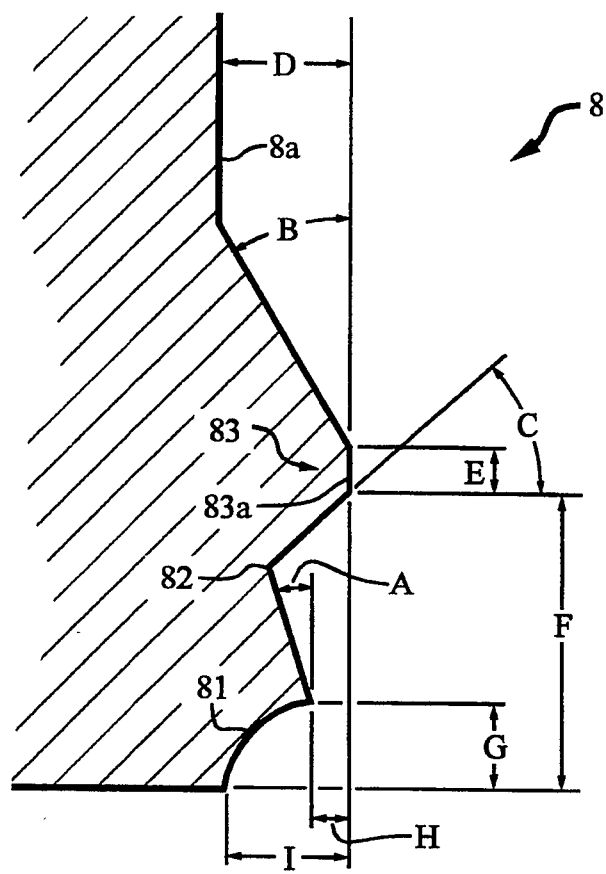
FIG. 4 is a sectional side view of the knifing section of a mold half of the blowmolding mold of the present invention.

As previously noted, the molds used in conventional blowmolding applications are not well-suited for use in the blowmolding of memory plastic prosthetic socket preforms. A sectional side view of a typical knifing section of a conventional mold is shown in FIG. 3. In particular, the design of the knifing section of conventional molds results in the formation of an internal rib 12 in the preform 11 due to the location and geometry of the pinch-off zone 13. In recognition of this problem, the mold of the present invention offers a redesigned knifing section which avoids this problem as well as others associated with the use of conventional molds. The redesigned knifing section is typically needed at only the upper end of the mold 1 because the lower end of the preform is severed and because clamping of the parison 3 at the lower end is not as critical. FIG. 4 shows a sectional side view of the upper knifing section 8 of a mold half (1a or 1b) of the present invention. The upper knifing section 8 of each of the mold halves 1a and 1b includes a pinch-off zone 83 for severing the upper portion of the parison 3, a clamping zone 82 located below the pinch-off zone 83 for securing and retaining the parison 3 to the upper end of the mold halves 1a and 1b, and a well 81 located below the clamping zone 82 for receiving excess plastic at the upper portion of the parison 3 during the pinching process.

The pinch-off zone 83 comprises a flattened V-shaped ridge extending from the face 8a of upper knifing section 8 and terminating in flat surface 83a parallel to the face 8a. Because both mold halves have aligned surfaces 83a, such surfaces contact each other when the halves are fitted together, thereby severing the parison 3.

The clamping zone 82 comprises a V-shaped groove having its upper surface 82a also forming the lower surface of pinch-off zone 83. The clamping zone 82 offers a solution to the problem of premature parison severing, also associated with conventional molds, by providing a geometry for receiving and clamping plastic material of the parison 3 below the pinch-off zone 83. In a more preferred embodiment, the pinch-off zone 83 and clamping zone 82 extend substantially across the total width of the parison 3, which further minimizes the risk of parison severing by maximizing the amount of plastic material 5 retained in clamping zone 82 when the mold halves 1a and 1b are assembled.

The well 81 comprises semicircular notch 81a formed at the bottom edge of the upper knifing section 8. As previously pointed out, the well 81 allows the excess plastic material that previously formed an internal rib 12 using the prior art molds to instead form a external rib which would not impinge inwardly upon the residual limb and which is much easier to remove, if necessary.

In one embodiment, the mold 1 is machined from aluminum alloy and features steel knifing sections at the upper and lower ends. Steel backplates (not shown) are incorporated with the mold to facilitate mounting of the mold on the blowmolding apparatus and the mold is capable of inversion on its mountings. The dimensions of one particular embodiment of upper knifing section 8 are given in TABLE 2 using reference letters A-J from FIG. 4.

OPERATION

The blowmolding method of the present invention comprises the following steps: First, the mold 1 is aligned with the blowmolding apparatus as described above. Specifically, the mold halves 1a and 1b are axially aligned with the blow pin 6, the die 4a and the mandrel 4b. Next, a mass of memory plastic material 5, at a preselected temperature, is extruded for a preselected time through the die 4a and mandrel 4b to form a parison 3, the parison 3 extending between the mold halves 1a and 1b, through inner cavities 9, and terminating in an opening 3a past the lower end of the mold halves 1a and 1b. The preferred plastic supply means is capable of supplying plastic 5 under pressure at variable temperatures, as required for the optimal blowmolding of different plastics.

For example and without limitation, memory plastic materials which may be used include low density polyethylene ("LDPE") (Dow 682), linear low density polyethylene ("LLDPE") (7340), LDPE/LLDPE, very low density polyethylene ("VLDPE") (1137), VLDPE/LDPE, Surlyn (1601), K-Resin, and polypropylene. These are chosen in part for their high molecular weight and thus their high shrinkage characteristics upon reheating. Other materials with similar characteristics may also be used.

The length of the parison is controlled by the amount of time, designated as $t_e$, that the plastic 5 is extruded (the "extrusion time" or "parison push out time"). The extrusion times $t_e$ and parison temperatures $T_p$, the latter being measured by inserting a temperature probe into the wall 3b of parison 3, as presently used for selected plastics are given in TABLE 1. These values may change for different blowmolding machines. Also given in TABLE 1 are values for the temperature measured at the accumulator, crosshead and extruder head, listed as $T_x$, $T_y$ and $T_z$, respectively. (These are located upstream of the extruding assembly 4. They collect, hold and push the molten plastic 5 into the extruding assembly 4.)

After the parison 3 has been extruded to the desired length, the blow pin 6 may be inserted into the parison opening 3a and the mold halves 1a and 1b are moved or clamped together. In this configuration, the parison 3 is pinched at its upper portion by the pinch-off zone 83 of the upper knifing section 8 and is compressed at its lower portion around the blow pin 6 by the blow pin aperture halves 7 to form a substantially air-tight chamber within the parison 3.

Next, the parison 3 may be cooled for a preselected time. It is believed that the cooling step enhances the molded-in stresses in the resulting preform. In conventional blowmolding applications, such molded-in stresses are undesirable and the parison 3 is normally expanded immediately after closing the mold in order to minimize molded-in stresses. For the purposes of the present invention, however, this step is believed to be desirable. It is believed that large thermal shrinkage in thermoplastic preforms is promoted by high levels of molded-in stress due to chain orientation which is in turn increased by using a combination of relatively low processing temperatures and high molecular weight materials.

Such a cooling step may be achieved in a number of ways. First, the parison 3 may simply be allowed to remain undisturbed for up to one minute, or some other preselected time, at the ambient temperature within the inner cavities 9 of the mold 1, such temperature being lower than the rigid temperature of the parison. It is important that there should be no air leak into the parison during this stage, e.g., from the blow pin air pressurization system causing pressurization of the parison and premature expansion.

Figure 5:
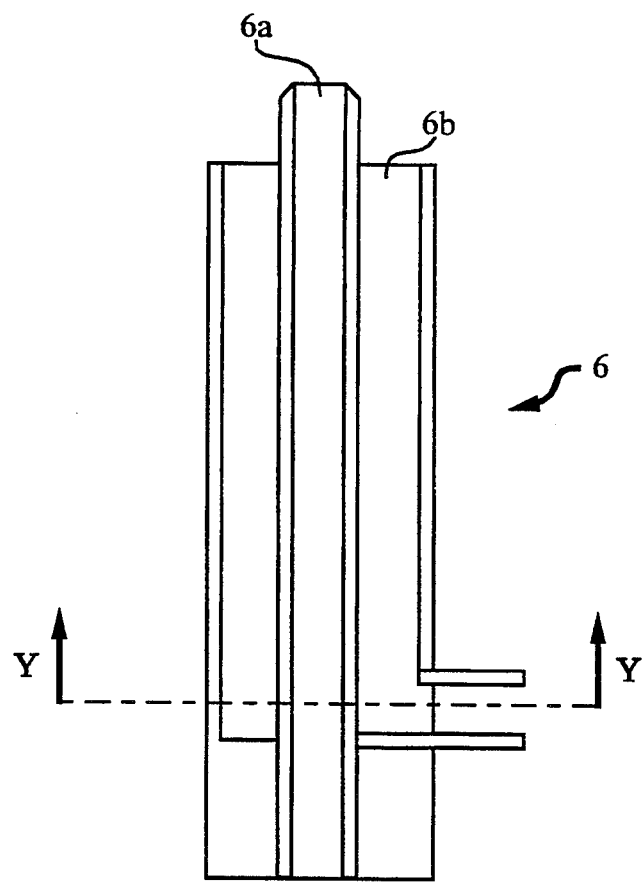
FIG. 5 is a sectional side view of the blow pin used in a particular embodiment of the blowmolding method of the present invention.
Figure 5A:
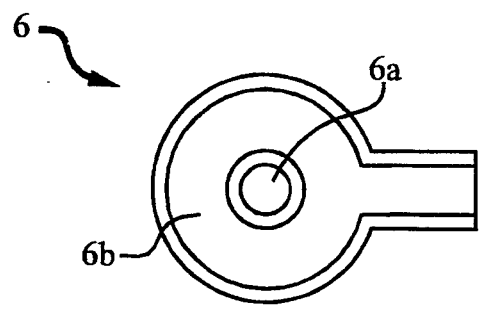
FIG. 5A is a sectional end view along section line Y—Y of the blow pin of FIG. 5.

More preferably, the parison 3 may be cooled at a more rapid rate by injecting air into the inner chamber of parison 3 as for example through a specially designed blow pin 6. A sectional side view of such a blow pin 6 is given in FIG. 5. FIG. 5A is a sectional end view along section line Y—Y of the blow pin of FIG. 5. The blow pin 6 of the preferred embodiment includes an inlet passage 6a for directly injecting air into the parison 3 and a selectively closeable outlet passage 6b concentric about the inlet passage 6a for allowing air to exit from the parison 3. In this embodiment, air is injected into the parison 3 at 2 psi or less for a preselected time $t_c$. This low pressure and the outlet passage 6b ensure that the parison 3 is not prematurely expanded during cooling. The cooling times (or "parison hold times") $t_c$ for selected plastics are given in TABLE 1. This air exits through outlet passage 6b, which is opened during this portion of the process.

After the cooling step is complete, the outlet passage 6b of blow pin 6 is closed (if such a pin 6 is used) and air is then injected through the blow pin 6 into the sealed parison 3 until the parison 3 has expanded to conform to the inner cavities 9 of the mold halves 1a and 1b, thus forming an unfinished socket preform of desired dimensions. In a particular embodiment, the air may be injected at approximately 30 psi for a time of about 90 seconds.

Figure 6:
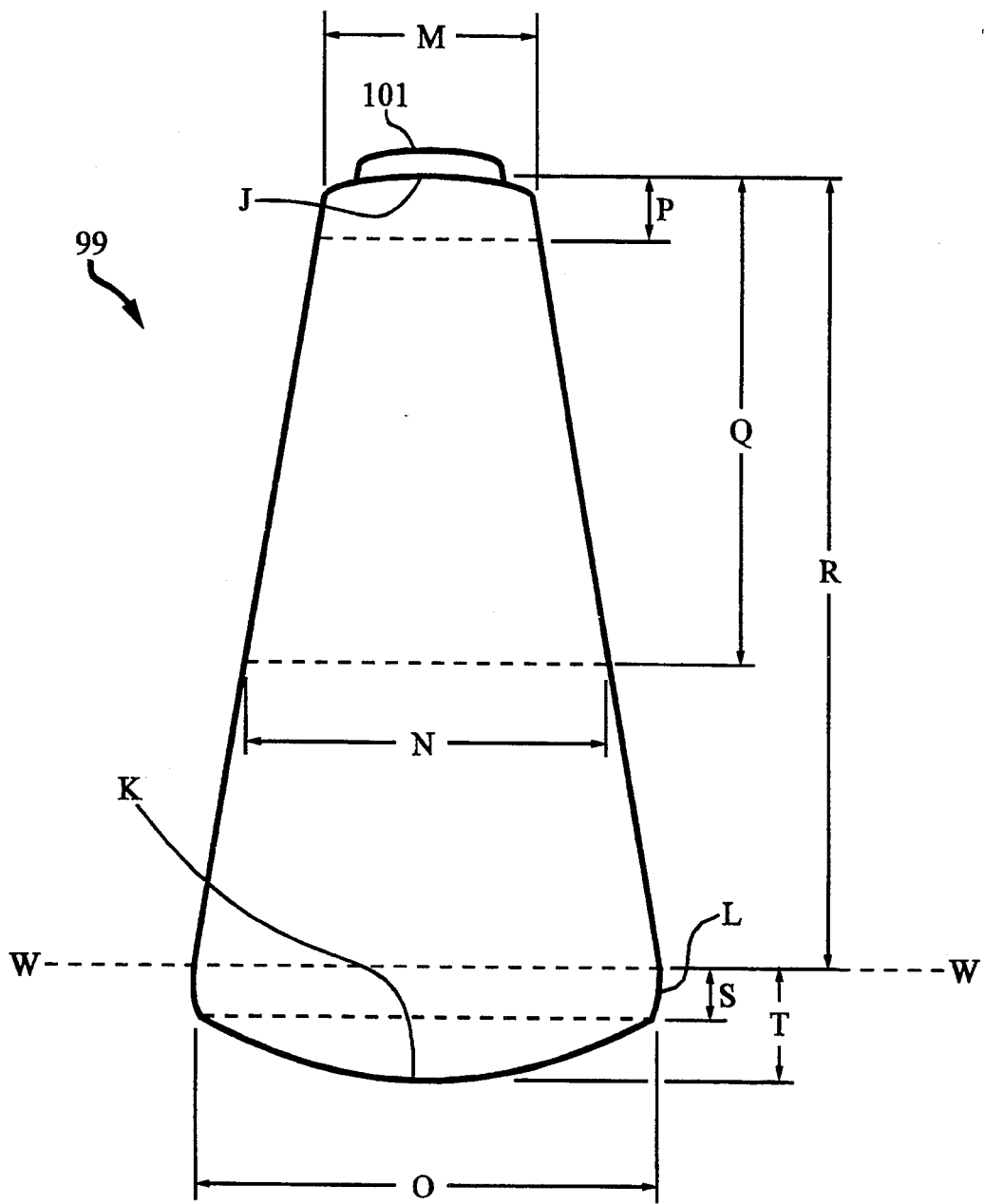
FIG. 6 is a side view of the unfinished preform produced by the blowmolding method of the present invention.
Figure 6A:
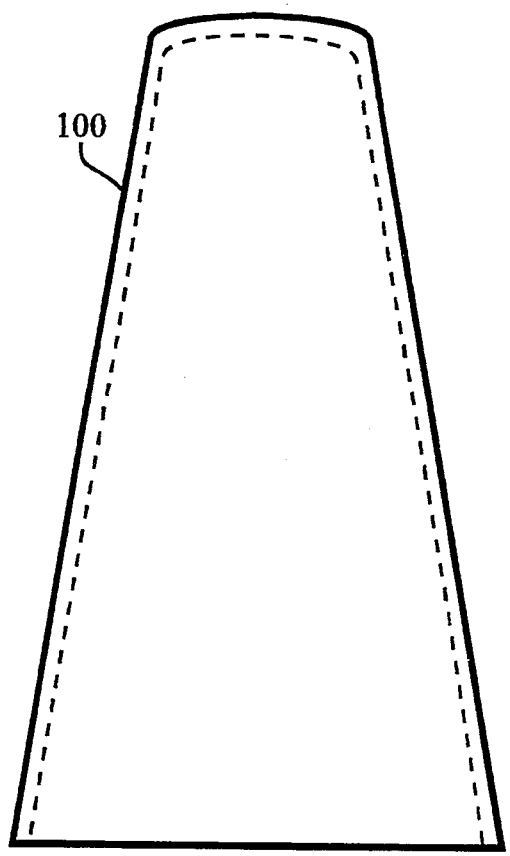
FIG. 6A is a side view of the preform produced by the blowmolding method of the present invention after finishing.

After parison expansion against the surface of inner cavities 9 is complete, the unfinished socket preform is allowed to cool for a preselected time in contact with the inner cavities 9. The mold halves 1a and 1b are then moved apart and the unfinished socket preform is removed. At this stage, the preform comprises a hollow, generally conical closed structure. The unfinished preform 99 is shown in FIG. 6. The presently used dimensions for below-knee and above-knee socket preforms are given in TABLE 3 corresponding to reference letters J through T in FIG. 6. (These dimensions also correspond to those of the inner cavities 9 of BK and AK preform molds 1 when the mold halves 1a and 1b are moved together.) The unfinished preform 99 is prepared for shrink-forming by removing any excess plastic, cutting or filing off the rib 101 which forms on the exterior of the preform at its upper end, and severing the lower portion of the preform along line W—W to form a generally conical finished preform 100, shown in FIG. 6A. The severing may be done with a band saw or the like. These finishing steps may be performed at the manufacturing facility or at the prosthetics laboratory.

Figure 7:
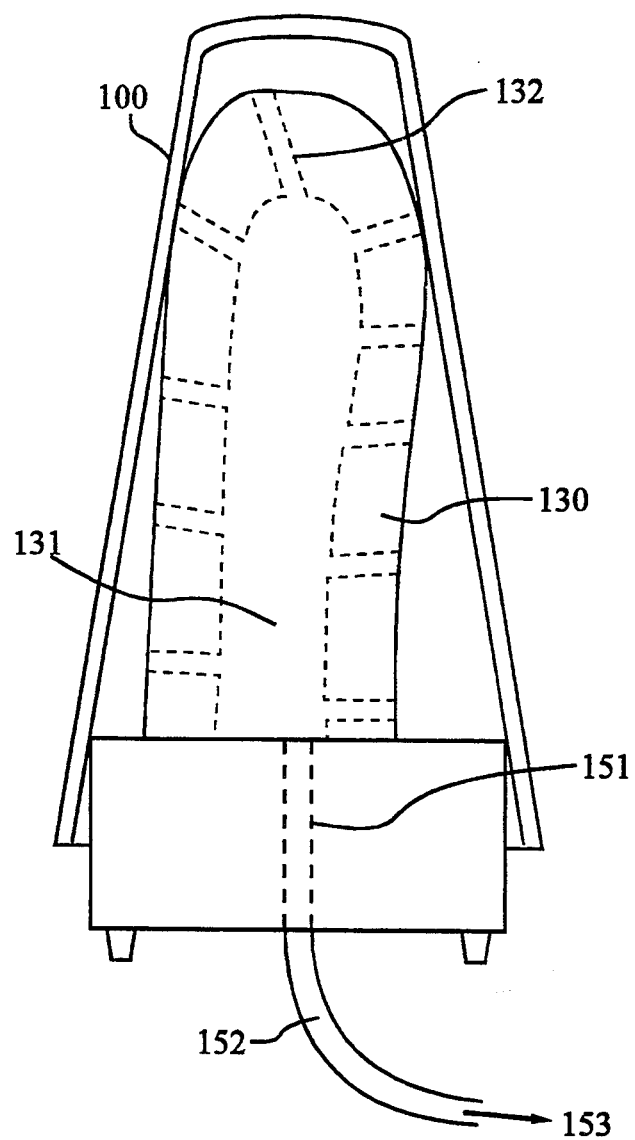
FIG. 7 is schematic view of the apparatus used in practicing the heat- and vacuum-forming method of the present invention.

Referring now to FIG. 7, a schematic illustrating one apparatus used in the heat- and vacuum-forming method of the present invention is given. The preforms 100 used should not exhibit yellowing or contamination by impurity particles such as dust specks, metal particles, or a different thermoplastic remaining in the barrel after purging. The practice of regrinding unacceptable blowmolded parts for reuse should not be employed as this can markedly affect processing conditions and shrinkage of the molding. Flow defects such as distinct flow lines or streaking, bubbles, stripes of localized thinning in the machine direction, transverse creases due to parison sag (except in the bottom 100 mm) or severe "shark skin" effects are to be avoided. As previously noted, there should be no pronounced internal rib at the smaller closed (upper) end of the preform 100. A substantially planar surface is required in this region, although a shallow groove is acceptable. The preform 100 should be dust-free before heat- and vacuum-forming.

The first step in the heat- and vacuum-forming method is to make a positive cast 130 of the end portion of the patient's residual limb. This may be accomplished by placing a residual limb sleeve over the residual limb, applying plaster to the sleeve, and letting the plaster dry. This forms a hollow "negative" cast of the residual limb. The negative cast, which now forms the inner surface of the negative cast, is then filled with plaster and a internal shaft is inserted into the cast cavity. After the plaster hardens, the negative cast and the internal shaft are removed, leaving a positive cast 130 of the residual limb having an inner chamber or cavity 131 open to the base of the cast. Certain regions of the cast may need to be built up or custom formed in order to create a biomechanically correct socket contour. For example, in a below-knee socket, the region of the socket impacting the patellar tendon must include a protuberance to prevent damage to the limb during use. Therefore, the positive cast, being the "negative" of the socket, must be custom formed at this point.

An alternative method of making the positive cast 131 is described in Walsh, et al, supra. This method involves the use of a computer aided design/computer aided manufacture ("CAD/CAM") system. In particular, a three-dimensional topographical record of the residual limb is obtained and stored in a computer using a camera/laser imaging system, the data is adjusted using computer software to create a biomechanically correct socket contour, and then the positive cast is created from a plaster "blank" using the modified data and a computer controlled lathe such as an ABT Carve Form.

After the positive cast 130 is prepared, a drill may be used to create a series of holes 132 distributed over the exterior surface of the cast 130 in communication with the inner chamber 131. The next step involves preheating the cast 130 in an oven (not shown). The cast 130 is placed on a vacuum forming platform 150 during preheating. This preheating minimizes the temperature differential between the cast 130/platform 150 and the preform 100 and thus avoids the heat-sinking effects of the prior art. Typically, the preform 100 is heated for about five minutes.

After preheating the cast 130, the preform 100 is placed over the cast 130 and these are heated in an oven to shrink the preform 100 over the exterior surface of the cast 130. In a preferred embodiment, an infra-red oven having evenly distributed radiation sources may be used, which offers a significant improvement in heating uniformity over conventional ovens. Such an oven has been custom-made for this purpose by DRI Clime Corp., Greenburg, Ind.

After removing the cast 130 and preform 100 from the oven, a partial vacuum may be applied to the inner chamber 131 of the cast 130 to further draw the preform 100 into contact with the exterior surface of the cast 130 to form a prosthetic socket having the desired interior contours. (Although the heating and vacuum steps are presently consecutive, these steps could be performed contemporaneously.) In order to create the desired vacuum at the interface of the cast 130 and the preform 100, the cast 130 is placed on the platform 150 with the inner chamber 131 in communication with a passage 151, which has an opening on the upper surface of the platform 151. Suction is applied to the passage 151 through tube 152 connected to a vacuum means 153 (not shown). In this configuration, a partial vacuum is thus applied to the region between the preform 100 and the cast 130 through the holes 132. The conforming of the preform 100 to the surface of cast 130 may be assisted manually if necessary. After the preform 100 has fully conformed to the contours of the positive cast 130 thereby creating an unfinished socket, it is removed from the cast, cleaned, excess plastic is cut away, and the edges are smoothed, creating a finished prosthetic socket.

Figure 8:
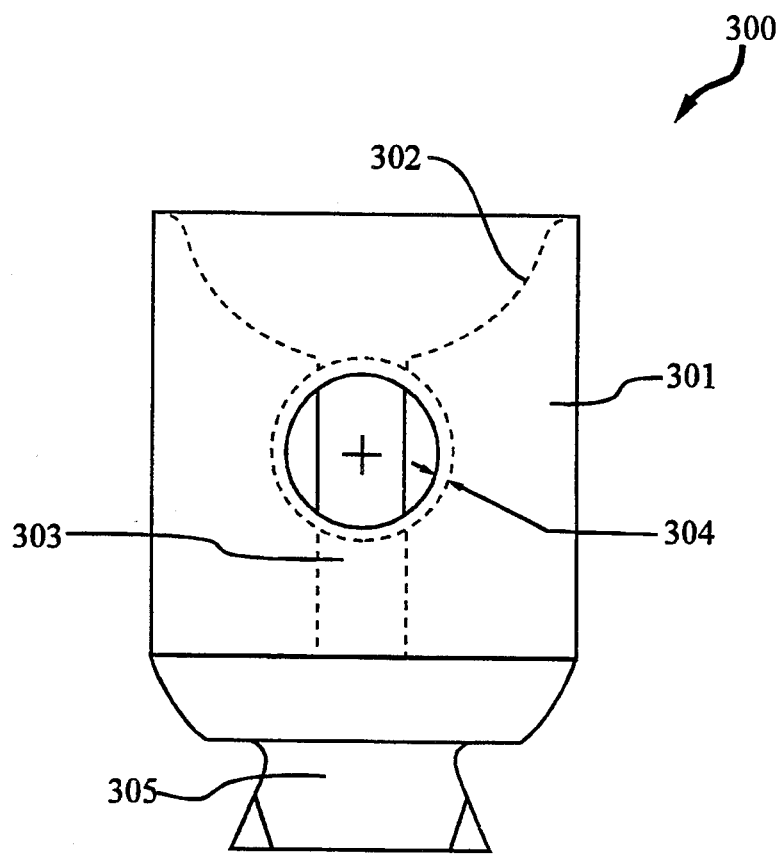
FIG. 8 is a side view of the socket attachment component of the present invention.
Figure 9:
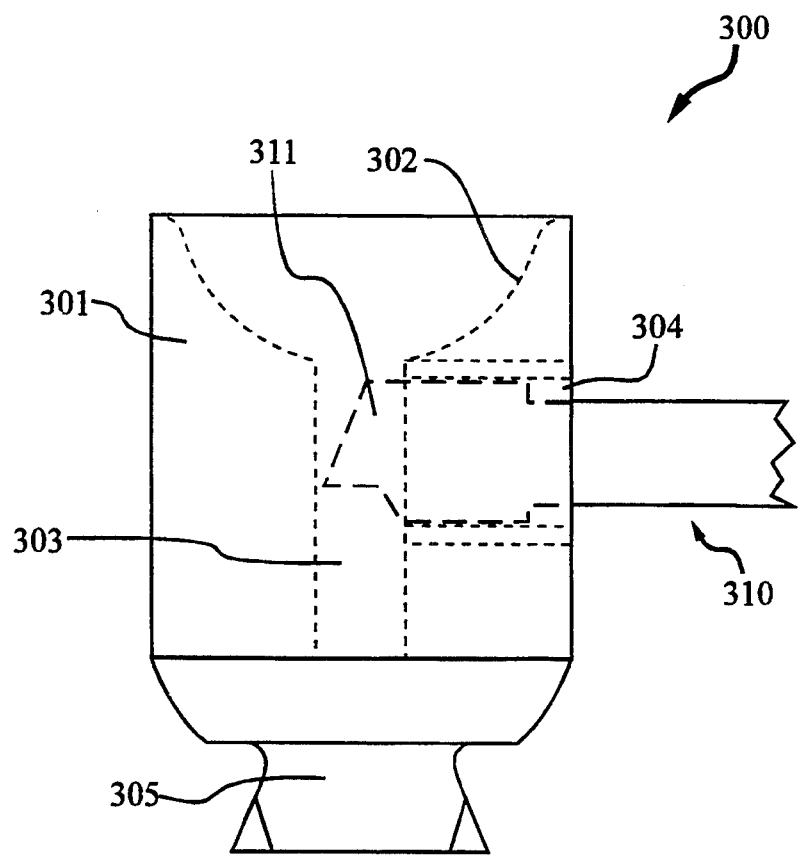
FIG. 9 is a side view the socket attachment component of FIG. 8 rotated 90°.

Referring to FIGS. 8 and 9, a particular embodiment of the socket attachment component 300 of the present invention is shown. The component 300 may be integrally molded with a prosthetic socket for attaching the prosthetic socket to an artificial limb shaft and for attaching the socket to a residual limb sleeve by means of a sleeve attachment shaft connected to the sleeve. FIG. 8 shows a side view of the socket component 300. A side view of the component 300 along section line V—V of FIG. 8 rotated 90° is given in FIG. 9. The component 300 includes a cylindrical body portion 301 having a hemispherical depression 302 in its upper surface, a first cylindrical hollow 303 extending downward from the center of the depression 302 and a second cylindrical hollow 304 intersecting and terminating at the first cylindrical hollow 303 and opening to the side surface of the body portion 301. The body may be knurled or textured on the outside to assist in adherence of the heated plastic material. The socket attachment component 300 has a connector or male member 305 extending from the lower surface of the body 301. In the particular embodiment shown in FIG. 8, the male member 305 comprises a frustum of substantially square cross-section, connected to body 301 opposite the frustum base, i.e., with the sides tapering outwardly from the body 301. This shape facilitates attachment to the artificial limb shaft. Connectors 305 of other shapes, such as a female member, may also be used, and the body 301 and connector 305 may be formed of aluminum, titanium or other lightweight material of sufficient strength.

Figure 10:
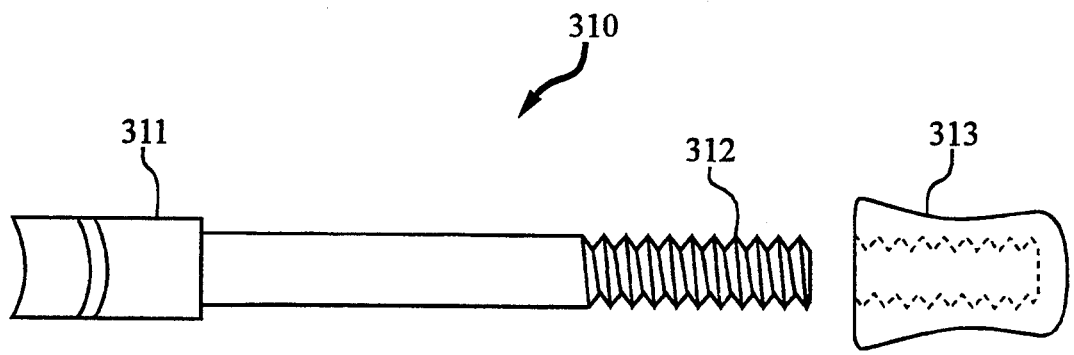
FIG. 10 is a side view of the pin of the socket attachment component of the present invention.
Figure 10A:
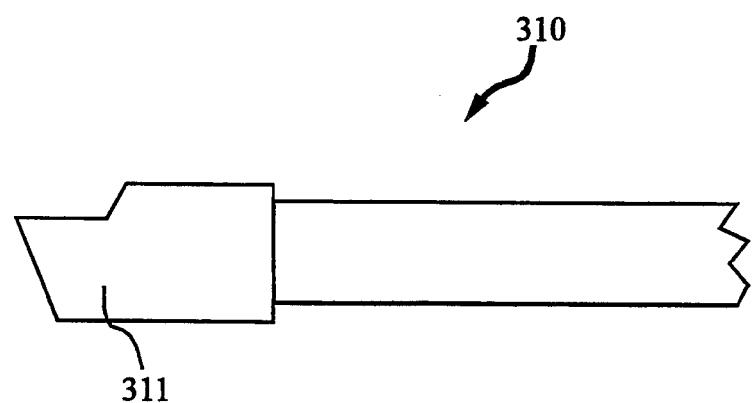
FIG. 10A is a top view of the pin of the socket attachment component of the present invention.

Finally, the socket attachment component 300 may include a spring-loaded pin 310, shown in FIGS. 9 and 10. When socket attachment component 300 is in use, the pin 310, is disposed in the second hollow 304 of body 301, having a first end 311 located proximate the first hollow 303 for selectively engaging the notches of a sleeve attachment shaft 420 (shown in FIG. 11) extending from the wearer's residual limb and a second end 312 located outside the second hollow 304. The first end 301 may terminate in a curved edge to facilitate engaging a round sleeve attachment shaft 420. The second end 312 of pin 310 may include a knurled knob 313 which is attached to the second end 312 of pin 310 after forming component 300 with the socket.

The socket attachment component 300 may be integrally formed with the finished socket by placing the component 300 atop the positive cast 130, the male member 305 directed upward, under the preform 100, prior to shrink-forming. During heating, the preform 100 will conform not only to the contours of the cast 130 but also to the component 300, including male member 305, thus attaching the component 300 to the socket.

Figure 11:
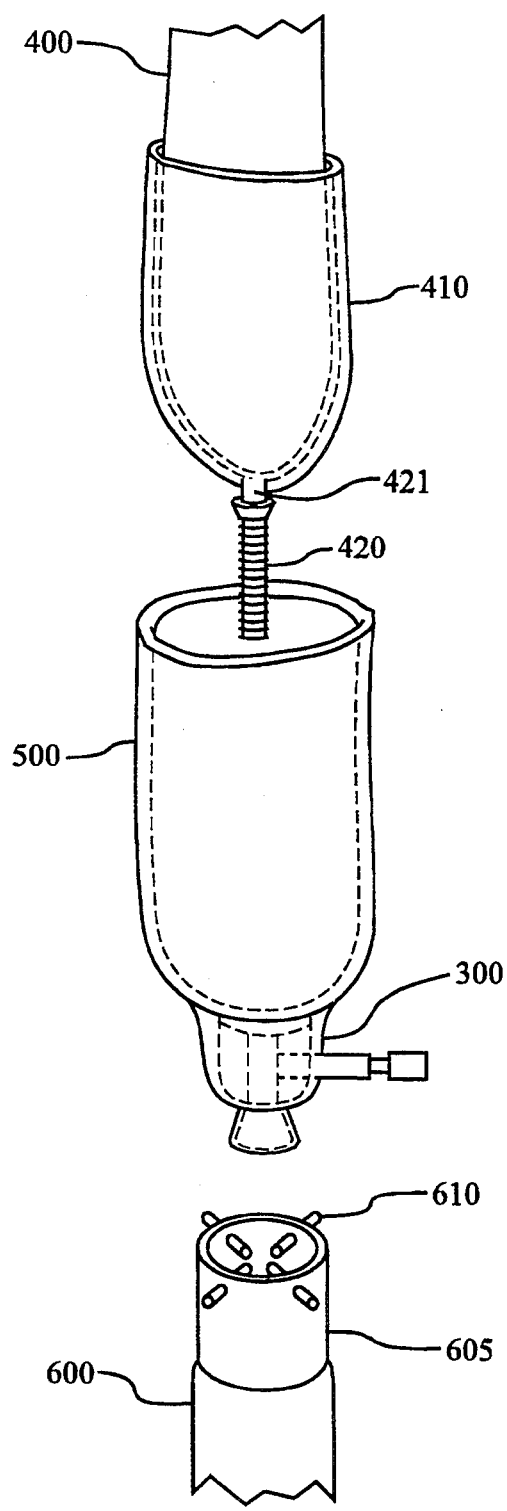
FIG. 11 is an exploded isometric view illustrating the means of securing the residual limb to an artificial limb shaft using the socket attachment component of the present invention molded with a prosthetic socket.

FIG. 11 is an exploded schematic view of the socket attachment component 300 in use illustrating the relationship of the various components. In fitting a patient with a prosthesis incorporating the socket attachment component 300 of the present invention, an elastic limb sleeve 410 is placed over the patient's residual limb 400, forming a partial vacuum with the limb 400 for securing the sleeve 410 to the limb 400. A sleeve attachment shaft 420 is connected to the end of the limb sleeve 410, typically by screwing it into a nut 421 formed with the sleeve 410. The sleeve attachment shaft 420 has a series of circumferential notches cut into its surface. The limb 400, the sleeve 410 and sleeve attachment shaft 420 are then inserted into the formed prosthetic socket 500, which has a socket attachment component 300 integrally formed at its lower (closed) end. As the sleeve attachment shaft 420 is inserted into the first hollow 303 of the socket attachment component 300, the spring-loaded pin 310 is partially retracted out of the first hollow 303. After the sleeve attachment shaft 420 is fully inserted into the first hollow 303 of the socket attachment component 300, the spring-loaded pin is released, which allows it to engage a notch in the sleeve attachment shaft 420, thus locking the sleeve 410 and sleeve attachment shaft 420 into place. The nut 421 fits within the depression 302 of the socket component 300.

The socket 500 may in turn be attached to an artificial limb shaft 600 by any appropriate means as for example through the use of a plurality of bolts or screws 610 mounted in holes in the wall of an adaptor 605 mounted at the upper end of the limb shaft 600, the bolts or screws radially extending into the interior of the socket adaptor 605. In particular, the male member 305 of socket attachment component 300, being molded with the socket 500, is inserted into an opening at the end of the adaptor 605 and the bolts or screws 610, distributed about the circumference of adaptor 605, are tightened into secure contact with the male member 305. The inverse tapered shape of male member 305 aids in securing the socket 500 to adaptor 605.

Further modifications and alternative embodiments of the apparatus of this invention will be apparent to those skilled in the art in view of the foregoing description. Accordingly, this description is to be construed as illustrative only and is for the purpose of teaching those skilled in the art the manner of carrying out the invention. It is to be understood that the forms of the invention herein shown and described are to be taken as the presently preferred embodiments. Various changes may be made in the shape, size and arrangement of parts. For example, equivalent elements or materials may be substituted for those illustrated and described herein, parts may be reversed, and certain features of the invention may be utilized independently of other features, all as would be apparent to one skilled in the art after having the benefit of this description of the invention. The present invention is therefore intended to embrace all alternatives, modifications and variations as fall within the spirit and broad scope of the appended claims.

TABLE 1

| Material | Temp. Setting (IF) | | | | | | Perform Wall Thickness (mm) |
|---|---|---|---|---|---|---|---|
| | $T_x$ | $T_y$ | $T_z$ | $T_p$ | $t_e$ | $t_c$ | |
| AK MOLDINGS | | | | | | | |
| LDPE (Dow682) | 340 | 340 | 340 | 340 | 6 | 8 | 3 |
| LLDPE (7340) | 360 | 360 | 360 | 359 | 15 | 15 | 2.5 |
| LDPE/LLDPE | 360 | 360 | 360 | — | 15 | 15 | 2.5 |
| VLDPE (1137) | 340 | 340 | 340 | — | 20 | 5 | 3 |
| VLDPE/LDPE | 400 | 400 | 400 | — | 15 | 5 | 2.5 |
| HDPE | 330 | 340 | 340 | 340 | 6 | 9 | 3 |
| Surlyn (1601) | 310 | 310 | 310 | 340 | 15 | 5 | 3 |
| K-resin | 350 | 350 | 350 | 360 | 5 | 0 | 3 |
| K-resin | 380 | 380 | 380 | 375 | 5 | 5 | 3.5 |
| Polypropylene | 360 | 360 | 370 | 382 | 8 | 30 | 2.5 |
| BK MOLDINGS | | | | | | | |
| LDPE | 340 | 340 | 340 | 350 | 6 | 15 | 3 |
| LDPE/LLDPE | 340 | 340 | 350 | 353 | 7 | 15 | 1.6 |
| K-resin | 340 | 360 | 350 | — | 5 | 0 | 3 |

TABLE 2

| Ref. | Dimension |
|---|---|
| A | 10° |
| B | 45° |
| C | 45° |
| D | 5 mm |
| E | 1 mm |
| F | 7 mm |
| G | 2 mm |
| H | 1 mm |
| I | 4.5 mm |

TABLE 3

| Ref. | BK | AK |
|---|---|---|
| J | r130 | r130 |
| K | r190 | r250 |
| L | r107.5 | r120 |
| M | 90 | 125 |
| N | 165 | 225 |
| O | 215 | 242 |
| P | 25 | 25 |
| Q | 250 | 400 |
| R | 400 | 475 |
| S | 30 | 30 |
| T | 58 | 58 |

(all in mm; r ~ radius)

What is claimed is:

1. A socket attachment component for attaching a prosthetic socket to an artificial limb shaft and for attaching said socket to a residual limb sleeve by means of a sleeve attachment shaft connected to said sleeve, said component comprising:

a cylindrical body having an upper surface and a side surface, said upper surface having a depression, a first cylindrical hollow extending downward from a center of said depression for receiving said sleeve attachment shaft, and a second cylindrical hollow intersecting said first cylindrical hollow and opening to the side surface of said body;

a spring loaded pin assembly disposed in said second hollow having a first end located proximate said first hollow for selectively engaging said sleeve attachment shaft and a second end located outside said second hollow; and a connector integrally formed with said body for attaching said socket to said limb shaft;

said socket attachment component being configured to be integrally molded with said socket.

2. The socket attachment component of claim 1 wherein said connector comprises a male member.

3. The socket attachment component of claim 1 wherein said connector comprises a female member.

4. The socket attachment component of claim 1 wherein said side surface of said cylindrical body is knurled.

5. The socket attachment component of claim 1 wherein said side surface of said cylindrical body is textured.

6. A method of making a prosthetic socket for attachment to an artificial limb shaft, said method comprising:

providing a positive cast of a patient's residual limb;

providing a socket attachment component, said component comprising a cylindrical body having an upper surface and a side surface, said upper surface having a depression, a first cylindrical hollow extending downward from a center of said depression for receiving said sleeve attachment shaft, and a second cylindrical hollow intersecting said first cylindrical hollow and opening to the side surface of said body; a spring loaded pin assembly disposed in said second hollow having a first end located proximate said first hollow for selectively engaging said sleeve attachment shaft and a second end located outside said second hollow; and a connector integrally formed with said body for attaching said socket to said limb shaft; said socket attachment component being configured to be integrally molded with said socket;

providing a plastic preform;

preheating the positive cast;

placing the socket attachment component atop the positive cast;

placing the plastic preform over the positive cast and the socket attachment component;

heating the plastic preform, the positive cast and the socket attachment component; and vacuum-forming the plastic preform over the socket attachment component and the positive cast to form a prosthetic socket.

* * * * *